United States Patent [19]

McDonald, Jr.

[11] Patent Number: 5,069,222

[45] Date of Patent: Dec. 3, 1991

[54] RESPIRATION SENSOR SET

[76] Inventor: Lewis D. McDonald, Jr., 701-17th Ave., Seattle, Wash. 98122

[21] Appl. No.: 575,597

[22] Filed: Aug. 31, 1990

[51] Int. Cl.⁵ ............................................... A16B 5/08
[52] U.S. Cl. ..................................... 128/724; 128/725
[58] Field of Search ...................... 128/716, 724, 725

[56] References Cited

U.S. PATENT DOCUMENTS

| | | | |
|---|---|---|---|
| 3,232,288 | 2/1866 | Kroboth | 128/724 |
| 3,403,876 | 9/1968 | Harris | 128/724 |
| 3,884,219 | 5/1975 | Richardson et al. | |
| 4,453,552 | 6/1984 | Ensign | |
| 4,763,663 | 8/1988 | Uphold et al. | |
| 4,777,963 | 10/1988 | McKenna | 128/724 |

FOREIGN PATENT DOCUMENTS

| | | |
|---|---|---|
| 2807357 | 2/1977 | Fed. Rep. of Germany . |
| 63-11133 | 7/1986 | Japan . |
| 542511 | 1/1977 | U.S.S.R. . |
| 1110440 | 2/1983 | U.S.S.R. . |
| 940743 | 10/1990 | U.S.S.R. . |
| 2039741 | 8/1980 | United Kingdom . |

Primary Examiner—William E. Kamm
Assistant Examiner—Scott R. Akers
Attorney, Agent, or Firm—Christensen, O'Connor, Johnson & Kindness

[57] ABSTRACT

A sensor set (10) is disclosed for use with a monitor (14) to monitor the respriation of an individual (12). In one arrangement, the sensor set includes a pair of spaced-apart parallel nasal thermocouple junctions (24 and 26) and an oral thermocouple junction (28) aligned with one of the nasal thermocouple junctions. These junctions are supported by a support structure (18) and are coupled to the monitor by a lead set (20) and connector set (22). The sensor set is easily positioned on the individual's upper lip by looping the lead wires over the individual's ears and securing them underneath the individual's chin. The individual's respiration produces a temperature difference between the thermocouple junctions and a cold or reference junction (69), producing an output that is sensed by monitor 14 to indicate respiration. An alternative configuration employs thermistors as the sensor elements.

15 Claims, 4 Drawing Sheets

RESPIRATION SENSOR SET

FIELD OF THE INVENTION

This invention relates generally to medical sensors and, more particularly, to respiration sensors.

BACKGROUND OF THE INVENTION

The respiration of an individual or patient may be monitored for a variety of reasons. For example, knowledge about a patient's respiration may assist a physician in assessing the patient's stability during surgery and recovery after surgery. Another rapidly growing field in which information about an individual's respiration may be of value is the field of sleep therapy.

Sleep therapy frequently involves, in part, the monitoring and analysis of an individual's respiration to improve the individual's sleep patterns. For example, when some individuals are asleep, their respiration becomes so erratic that they are frequently awakened from their sleep. In some instances, these awakenings may occur so often that the individual is left exhausted in the morning. Given the brief nature of the awakenings, however, they may not even be remembered. As a result, the nature of the sleep disorder may go undiagnosed. By monitoring the individual's respiration during the course of the night, however, the nature of the problem may be readily identified and treated.

A variety of techniques have been developed for use in monitoring respiration. Of particular interest, however, is an approach that senses the temperature of the air inhaled and exhaled by the individual. As will be appreciated, in most environments, the air breathed in by the individual will be at a lower temperature than the air breathed out. Thus, by monitoring temperature changes occurring in the individual's respiration path, an indication of respiration can be obtained.

Several different types of sensors are often used in thermal respiration monitoring systems. For example, either a thermistor or thermocouple can be employed as the temperature-sensitive element. Addressing first the thermistor-based system, a thermistor is a device whose resistance changes with temperature. A thermistor-based respiration monitoring system typically includes a thermistor, positioned in the respiration path, and a monitor that applies, for example, a small voltage to the thermistor. As the individual breathes, the temperature of the thermistor changes, causing the thermistor's resistance to change and altering the current flowing through the thermistor. The monitor then senses the current change and translates it into an indication of the change in respiration.

Unlike a thermistor, a thermocouple actually generates a thermoelectric potential that is proportional to the temperature difference between a pair of thermocouple junctions. A thermocouple-based respiration monitoring system employs a "hot" thermocouple junction in the individual's respiration path and a "cold" thermocouple junction outside the respiration path. These junctions produce a thermoelectric potential that is proportional to the temperature difference between the junctions. The thermocouple-based respiration monitoring system includes a monitor that translates changes in the thermoelectric potential generated between the junctions directly into a indication of respiration.

Regardless of whether the thermal respiration monitoring system employs a thermistor or thermocouple as the temperature-sensitive element, conventional system typically employ only one such sensor. For example, a single respiration sensor is often taped to the individual's upper lip in the path of inhaled and exhaled air. Alternatively, arrangements have been developed in which a single sensor is supported in the respiration airflow path by a device that is partially received within the individual's mouth.

Unfortunately, conventional thermal respiration-monitoring systems have a number of shortcomings. For example, many such systems employ sensor assemblies that are relatively complex, including detailed structures for channeling airflow and supporting the sensor element. The complexity of such sensor assemblies also results in relatively high sensor cost.

Further, because conventional systems typically employ a single sensor, they are often only partially effective at sensing respiration. In that regard, respiration may pass through the individual's mouth or one or the other of the individual's two nostrils, or some combination of these passageways. As a result, a single sensor positioned, for example, in front of the individual's mouth may be unable to detect respiration from the nostrils.

In addition sensors used to monitor the respiration of a sleeping individual are often bulky or must be taped to the individual's face. As will be appreciated, in addition to being uncomfortable, sensors constructed in this manner and for use in sleep therapy may easily interfere with the individual's sleep and, hence, the respiration pattern to be monitored.

In view of these observations, it would be desirable to provide a sensor, for use with a thermal respiration-monitoring systems, that is simple, inexpensive, and responsive to various alternative airflow paterns and that does not interfere with the sleep of an individual whose respiration is being monitored.

SUMMARY OF THE INVENTION

In accordance with this invention, a sensor, coupleable to a monitor, is disclosed for sensing the respiration of an individual. The sensor includes first and second respiration-responsive elements, exposable to the individual's respiration, for responding to the respiration. A connection device is provided for coupling the first and second respiration-responsive elements to the monitor and allowing the monitor to produce an output representative of the respiration that the first and second respiration-responsive elements are for responding to.

The respiration to be sensed by the monitor includes respiration through at least one nasal passageway and an oral passageway. The first respiration-responsive element is positionable adjacent the nasal passageway and a second-respiration-responsive element is positionable adjacent the oral passageway. A third respiration-responsive element, exposable to the individual's respiration, may also be included for responding to the respiration. With the respiration to be sensed by the monitor, including respiration through a pair of nasal passageways, the first and third respiration-responsive elements are positionable adjacent separate ones of the nasal passageways.

In accordance with a more particular aspect of the invention, a respiration sensor set is disclosed for use in monitoring the respiration of a patient. The set includes a first temperature-sensitive element, second temperature-sensitive element, and third temperature-sensitive element. A support is provided for supporting the first and second elements in substantially spaced-apart, parallel alignment and for supporting the first and third temperature-sensitive elements in substantially axial alignment. At least one pair of electrically conductive leads is coupled to the first, second, and third temperature-sensitive elements. At least one pair of electrical connectors is coupled to the pair of electrically conductive leads. The first, second, and third temperature-sensitive elements are, alternatively, thermocouple junctions or thermistors.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
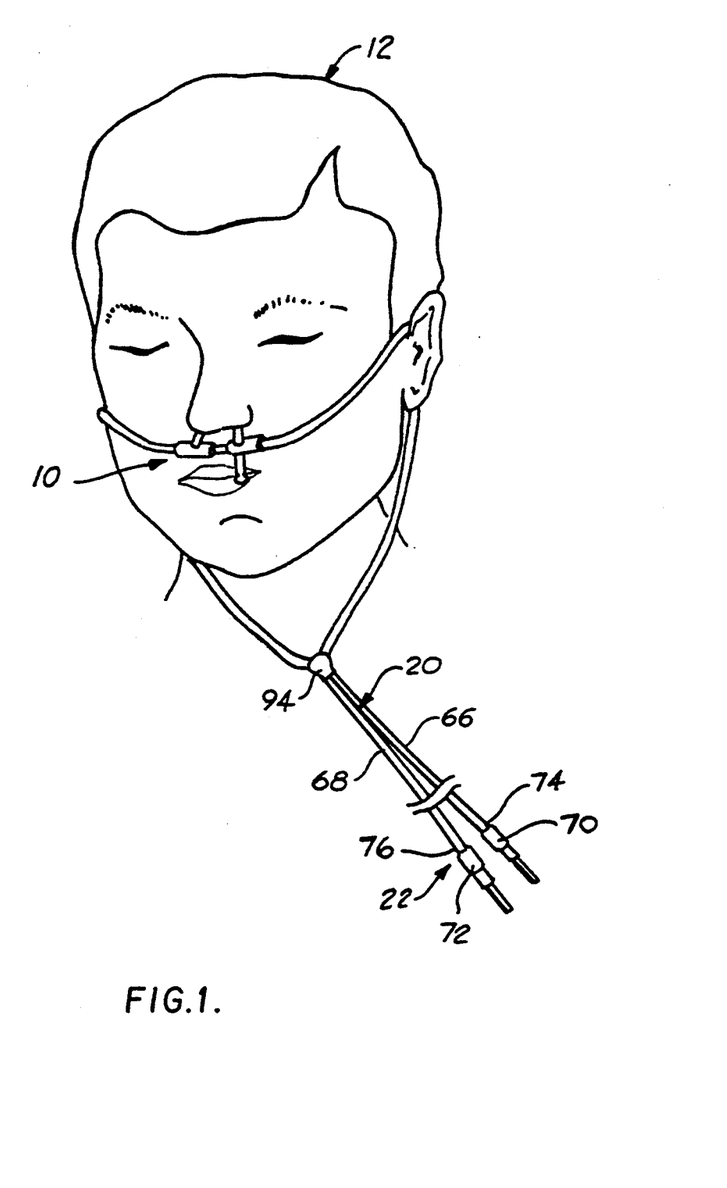
FIG. 1 illustrates a respiration sensor set, constructed in accordance with this invention, being worn by an individual whose respiration is to be sensed.

Referring now to FIG. 1, a respiration sensor set 10 constructed in accordance with this invention is shown positioned on the head of an individual 12 whose respiration is to be monitored. The sensor set 10 is coupled to a monitor 14, shown in FIG. 2, that produces an output representative of the individual's respiration. As will be described in greater detail below, the sensor set 10 is simple, inexpensive, easy to use, comfortable to wear, responsive to various alternative respiration flow patterns, and does not interfere with the sleep of an individual whose respiration is being monitored.

Figure 2:
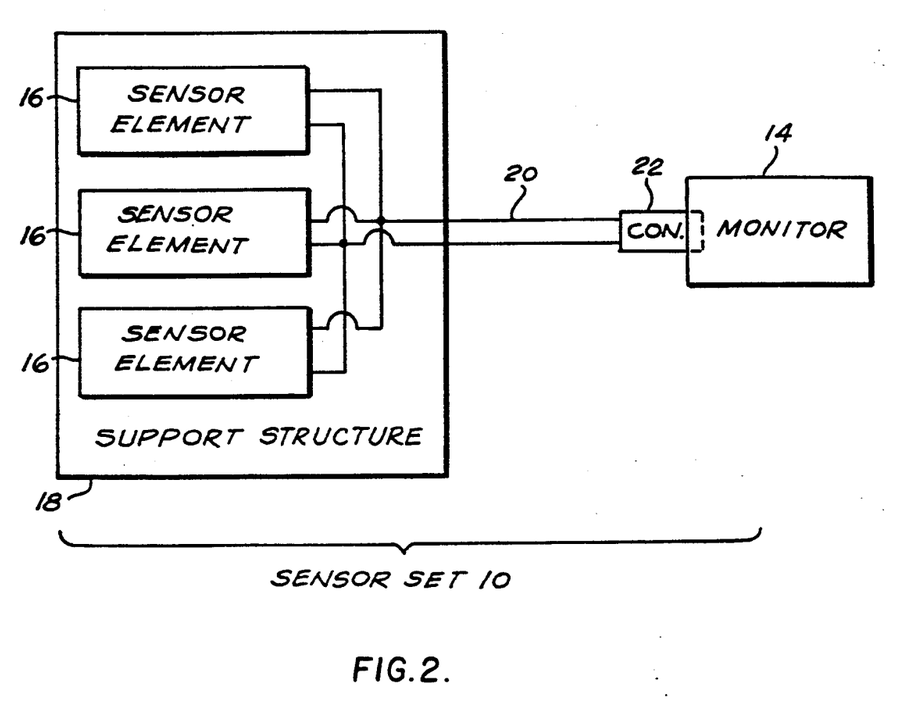
FIG. 2 is a block diagram of a respiration-sensing system employing the respiration sensor set of FIG. 1.

The sensor set 10 includes a plurality of sensor elements 16, a sensor housing or support structure 18, a lead set 20, and a connector set 22, all of which are shown schematically in FIG. 2. The sensor elements 16 may be any of a variety of devices suitable for sensing respired air, including temperature-sensitive, moisture-sensitive, and pressure-sensitive elements. The support structure 18 is included, in part, to help provide the desired relative alignment of the sensor elements 16. The lead set 20 and connector set 22 cooperatively allow the monitor 14 to determine the response of the sensor elements 16 to respiration from the individual 12.

Figure 3:
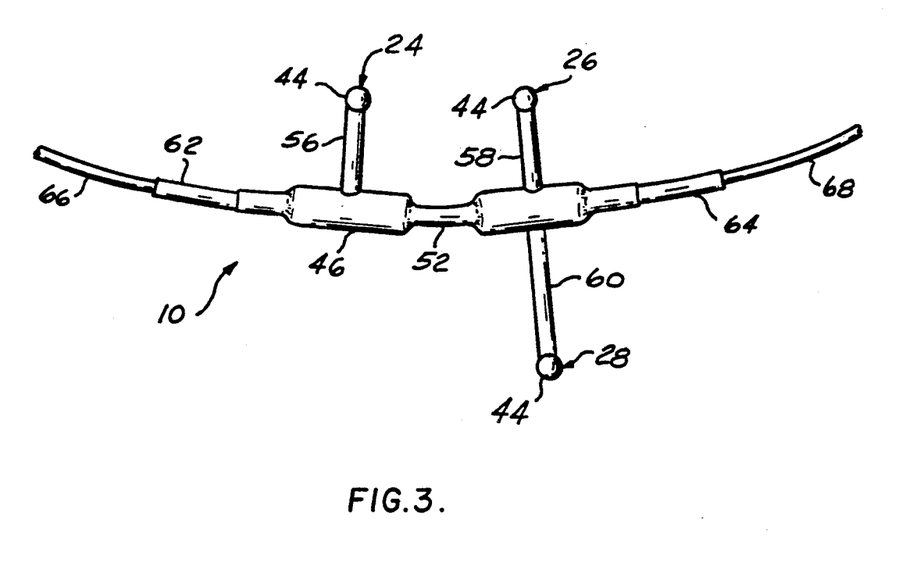
FIG. 3 is a more detailed illustration of a portion of the respiration sensor set of FIG. 1.
Figure 4:
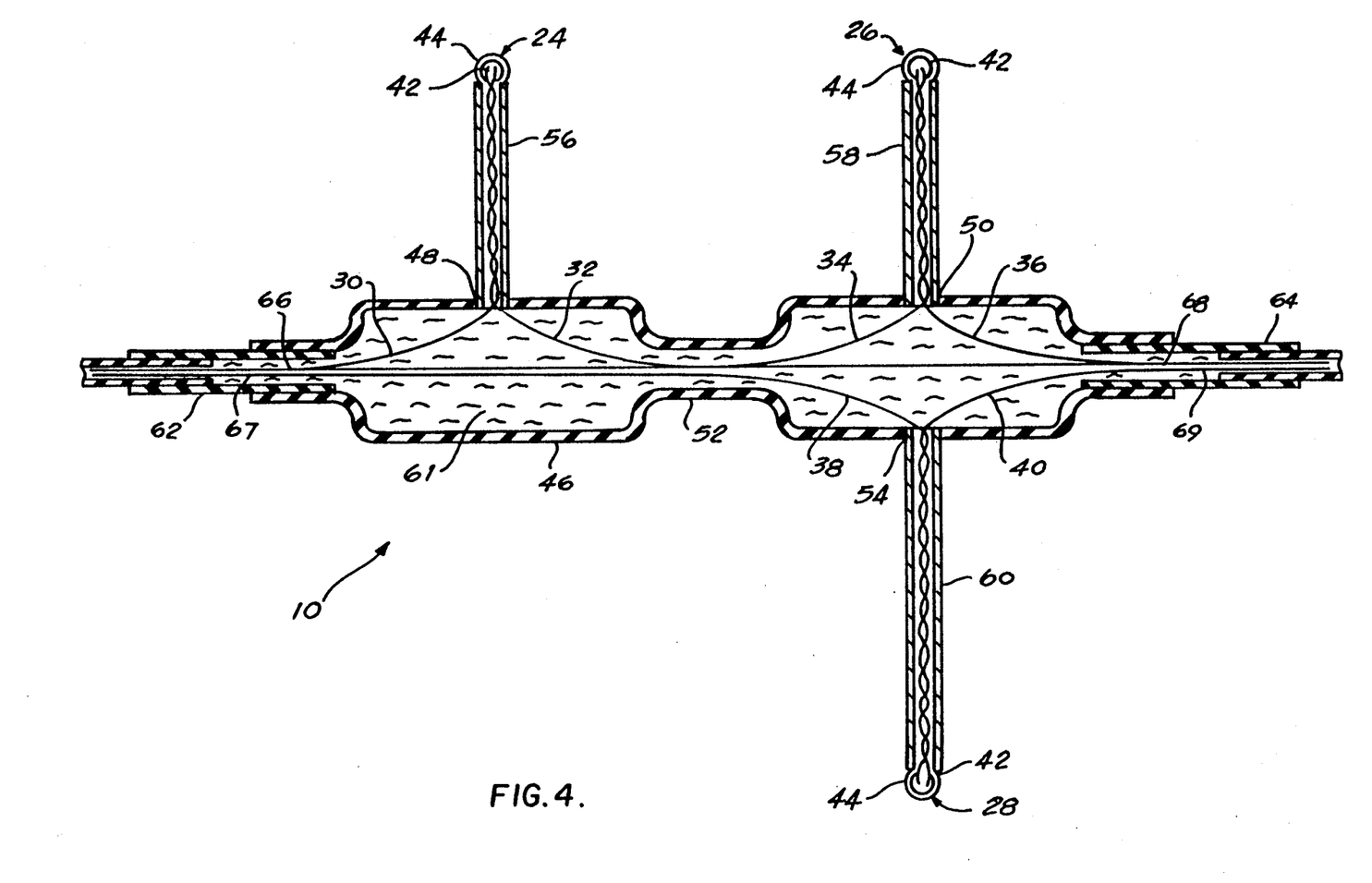
FIG. 4 is a sectional view of the portion of the respiration sensor set shown in FIG. 3.

Addressing now the various elements of the respiration sensor set 10 in greater detail, reference is had to FIGS. 3 and 4. As shown, the sensor set 10 includes three sensor elements 16 in the form of a first nasal thermocouple junction 24, second nasal thermocouple junction 26, and oral thermocouple junction 28. The first nasal thermocouple junction 24 is produced by twisting the ends of a first set of thermocouple wires 30 and 32. Similarly, the second nasal thermocouple junction 26 is formed by twisting the ends of a second set of thermocouple wires 34 and 36 together. The oral thermocouple junction 28 is likewise produced by twisting the ends of a third set of thermocouple wires 38 and 40 together.

In a preferred arrangement, the thermocouple wires 30 through 40 are ANSI Type T, paired 30-gauge thermocouple wires coated with a thermally conductive material such as that sold under the trademark Teflon. Each junction 24, 26, and 28 is coated with solder 42 to maintain the desired mechanical, electrical, and thermal connection between the junction wires. A bead 44 of thermally conductive material having a relatively low coefficient of friction, such as that sold under the trademark Teflon, is then provided over the tip of the soldered junctions 24, 26, and 28.

Junctions 24, 26, and 28 are effectively "hot" thermocouple junctions. As will be described in greater detail below, the thermoelectric potential generated between these junctions 24, 26, and 28 and a "cold" junction, included as part of the lead set 20 or monitor 14, is indicative of the temperature difference between the hot and cold junctions. With the hot junctions 24, 26 and 28 in the respiration path and the cold junction at an ambient temperature that remains relatively constant over brief intervals, this thermoelectric potential is generally proportional to the temperature of the air in the respiration path. As a result, this thermoelectric potential can be used to monitor respiration.

Addressing now the support structure 18 in greater detail, support structure 18 is included, in part, to protect the thermocouple wires 30 through 40 from damage or breakage. Structure 18 is also included to support the first and second nasal thermocouple junctions 24 and 26 in spaced-apart parallel alignment to each other, while supporting the second nasal thermocouple junction 26 and oral thermocouple junction 28 in roughly axial alignment to each other.

As shown in FIG. 4, the support structure 18 includes as its primary component a substantially tubular body 46 for receiving the "free" or untwisted ends of thermocouple wires 30 through 40. The main body 46 is generally 1.6 inches (4.1 centimeters) long, and 0.12 inch (0.3 centimeter) in outer diameter. In the preferred arrangement, body 46 is made of a tubular "shrink-wrap" material of the type sold by ICO-Rally Corp. of Palo-Alto, Calif., under the trademark HEATRAX.

Body 46 is provided with a pair of nasal sensor openings 48 and 50, approximately 0.06 inch (0.15 centimeter) in diameter and spaced roughly 0.8 inch (2.0 centimeters) apart. A portion of the first set of thermocouple wires 30 and 32, including junction 24, and a portion of the second set of thermocouple wires 34 and 36, including junction 26, project from body 46 through openings 48 and 50, respectively, at roughly right angles to body 46. A flexible, reduced-diameter portion 52 of body 46, having an outer diameter of 0.19 inch (0.5 centimeter) is located midway between two openings 48 and 50.

Axially aligned with nasal sensor opening 50 is an oral sensor opening 54 approximately 0.06 inch (0.15 centimeter) in diameter. The portion of the third set of thermocouple wires 38 and 40 including junction 28 projects through opening 54 at roughly a right angle from body 46 through opening 54.

The portions of the first set of thermocouple wires 30 and 32, second set of thermocouple wires 34 and 36, and third set of thermocouple wires 38 and 40 projecting from body 46 are generally received within, and supported by, additional tubular elements 56, 58, and 60. As shown in FIG. 4, tubular element 56 extends roughly from the first nasal sensor opening 48 in body 46 to the bead 44 on the first nasal thermocouple junction 24. Similarly, tubular element 58 projects from the second nasal sensor opening 50 in body 46 to the bead 44 on the second nasal thermocouple junction 26. Tubular element 60 likewise extends from the oral sensor opening 54 in body 46 to the bead 44 on the oral thermocouple junction 28.

The tubular elements 56, 58, and 60 are preferably made of the same material as body 46 but are of a smaller outer diameter, approximately 0.06 inch (0.15 centimeter), and lesser wall thickness. In the preferred arrangement, tubular elements 56 and 58 are roughly 0.4 inch (1.0 centimeter) long, while tubular element 60 is roughly 0.4 inch (1.0 centimeter) long, while tubular element 60 is roughly 0.5 inch (1.3 centimeters) long.

To further physically protect the thermocouple wires 30 through 40 received within the body 46 and tubular elements 56, 58, and 60, the body 46 is preferably filled with a flexible, nonconductive material 61. The material 61 completely encapsulates the wires 30 through 40 in body 46 and, at least partial, fills any spaces in the tubular elements 56, 58, and 60 as well. As will be appreciated, by electrically isolating the thermocouple wires 30 through 40, the material 61 also protects the individual 12 and monitor 14 in the event the sensor set 10 is exposed to fluid.

The final element of support structure 18 to be considered is a pair of strain relief tubes 62 and 64 that provide a flexible transition between the body 46 of the support structure 18 and the lead set 20. Tubes 62 and 64 are of the same general construction as the tubular elements 56, 58, and 60 discussed above, except that they are roughly 0.8 inch (2.0 centimeters) long.

As shown, the lead set 20 includes a pair of electrically conductive wires 66 and 68. Each wire 66 and 68 is preferably 48 inches (122 centimeters) long and made of 20 gauge stranded wire, provided with an insulative coating. As shown in FIG. 4, wires 30, 34, and 38 of the first, second, and third set of thermocouple wires 30 through 40 are connected to lead wire 66 at junction 67, while wires 32, 36, and 40 are coupled to lead wire 68 at junction 69. This is accomplished, for example, by soldering the adjacent ends of the thermocouple and lead wires.

The free ends of the lead wires 66 and 68 terminate in conventional pin plugs 70 and 72, respectively. As will be appreciated, pin plugs 70 and 72 allow electrical connections between the lead wires 66 and 68 and the monitor 14 to be made quickly and easily. Depending upon the design of the pin plugs 70 and 72, the connection between the lead wires 66 and 68 and pin plugs 70 and 72 may be provided mechanically or by soldering.

A flexible transition between the pin plugs 70 and 72 and lead wires 66 and 68 is also provided, in part, by strain relief tubes 74 and 76. Tubes 74 and 76 are preferably made of the same material as tubes 62 and 64 and are approximately 1.25 inches (3.2 centimeters) long.

Although not shown in FIG. 4, as will be appreciated, the requisite cold thermocouple junction may be located at any of a variety of positions, as long as it is connected in series with the hot junction or junctions with which it cooperatively produces thermoelectric potentials. For example, if thermocouple wires 30, 34, and 38 are made of copper, thermocouple wires 32, 36, and 40 are made of constantin or copper and iron, and lead wires 66 and 68 are made of copper, the connection between lead wire 68 and thermocouple wires 32, 36, and 40 provides a cold thermocouple junction 69. As will be appreciated, junction 69 is thermally isolated from the individual's respiration by the support structure 18. Thus, with the hot junctions 24, 26, and 28 exposed to the individual's respiration, a temperature differential would be established between the series-connected hot and cold junctions, causing a thermoelectric potential representative of the temperature difference to be applied to the monitor 14.

As will be appreciated, a sensor set 10 constructed in the preceding manner is a relatively simple, lightweight, inexpensive assembly. When positioned on the upper lip of individual 12, the two nasal thermocouple junctions 24 and 26 are positioned adjacent the individual's two nostrils, in the path of nasal respiration. Similarly, the oral thermocouple junction 28 is positioned adjacent the individual's mouth, in the path of oral respiration. Because thermocouple junctions 24, 26, and 28 are connected in parallel to the single set of lead wires 66 and 68, respiration at any one of the three thermocouple junctions 24, 26, and 28 may establish a thermoelectric potential with respect to the cold junction that allows the respiration to be detected. Thus, the sensor set 10 is responsive to alternative respiration flow paths.

The relatively flexible nature of the materials used to form the sensor set 10 allows the sensor set 10 to be conformed to the individual's face to optimize the positioning of the thermocouple junctions 24, 26, and 28 in the respiration flow paths. By conforming the sensor set 10 to the individual's face, the conformability of the sensor set 10 is also enhanced. Further, the beads 44 on each junction 24, 26, and 28 prevent the individual 12 from being scratched by the twisted ends of the pairs of wires 30 through 40, while the body 46, material 61, and tube 56, 58, and 60 provide the desired electrical isolation.

A monitor 14 that is suitable for use with a sensor set 10 of the type described above can be any one of a variety of devices for sensing the thermoelectric potential generated between the hot thermocouple junctions 24, 26, and 28 and a cold reference junction. Although in the preferred arrangement, the monitor 14 is an electroencephalograph (EEG), the monitor 14 may be a microprocessor-based device or system that is further capable of analyzing the received thermoelectric potential to provide an output representative of respiration. In that regard, fluctuations in the thermoelectric potential can be monitored to produce an indication of respiration rate. Further, with information concerning the cross-sectional respiration area available to monitor 14 in the form of, for example, operator-initialized data, the monitor 14 can be programmed to provide an output representative of respiration volume. In addition, monitor 14 may produce an indication of trends or patterns in the respiration rate or volume.

The monitor 14 may also include the requisite cold junction. For example in the event that the thermocouple wires 30 through 40 are employed as the lead wires 66 and 68 and extended to the monitor 14, the cold junction between dissimilar materials may be provided at the connection to monitor 14 or as an internal part of the monitor 14. If the monitor 14 further includes some calibration mechanism, such as an independent temperature-sensitive element, to determine the effective temperature of the cold junction, the monitor 14 can be designed to produce an indication of the actual temperature of the hot junctions 24, 26, and 28 in the respiration path, rather than just an indication of the temperature difference between the hot and cold junctions.

As will be appreciated, the construction of the sensor set 10 described above may vary substantially. For example, the thermocouple junctions 24, 26, and 28 may be replaced by thermistor junctions. The resistance of each thermistor junction will change as the temperature of the air in the respiration path changes. As a result, the monitor 14 must be constructed to interpret sensed resistance changes, rather than thermoelectric potentials, from the sensor set 10. Specifically, such a monitor 14 provides, for example, a voltage to the sensor set 10 and evaluates respiration by monitoring fluctuations in the current through the sensor set 10 caused by changes in the resistance of thermistors 24, 26, and 28.

As will be appreciated, the use of thermistors as the sensor elements 16 advantageously eliminates the need for a cold or reference junction or element. On the other hand, energy must be applied to a thermistor to determine the change in its resistance, while the use of a thermocouple configuration converts some of the thermal energy of respiration to electrical energy that can be monitored directly. As a result, the thermistor-based approached is less efficient.

Figure 5:
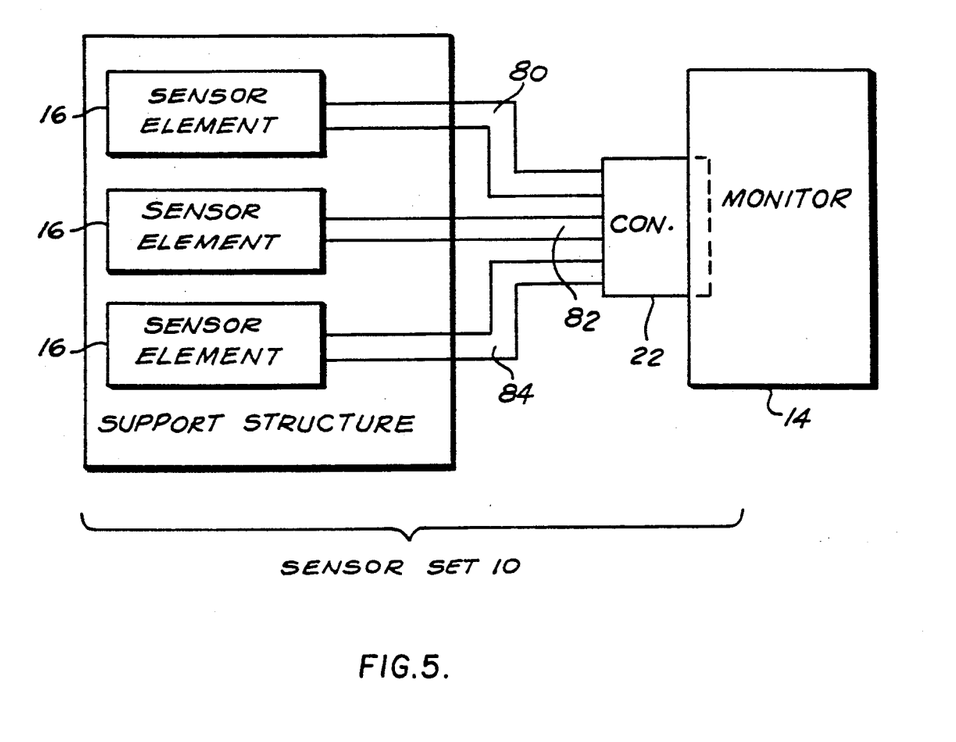
FIG. 5 is a block diagram of an alternative arrangement of the respiration-sensing system shown in FIG. 2; and, FIG. 6 is an illustration of an alternative embodiment of the portion of the respiration sensor set shown in FIG. 3.

Another variation of the basic sensor set 10 described above involves the coupling of each sensor element 16 to the monitor 14 through a separate pair of lead wires 80, 82, and 84 as shown schematically in FIG. 5. This arrangement can easily be produced by employing the thermocouple wires 30 through 40 as the pairs of lead wires 80, 82, and 84, extending the thermocouple wires 30 through 40 to the connector set 20. The connector set 22 coupled to the pairs of lead wires 80, 82, and 84 may be of any suitable construction for providing the equivalent of a six-pin connection to monitor 14. As will be appreciated, this arrangement advantageously allows monitor 14 to produce separate outputs indicative of the respiration sensed by individual ones of the sensor elements 16. As a result, the individual's respiration can be more closely monitored and diagnosed.

Figure 6:
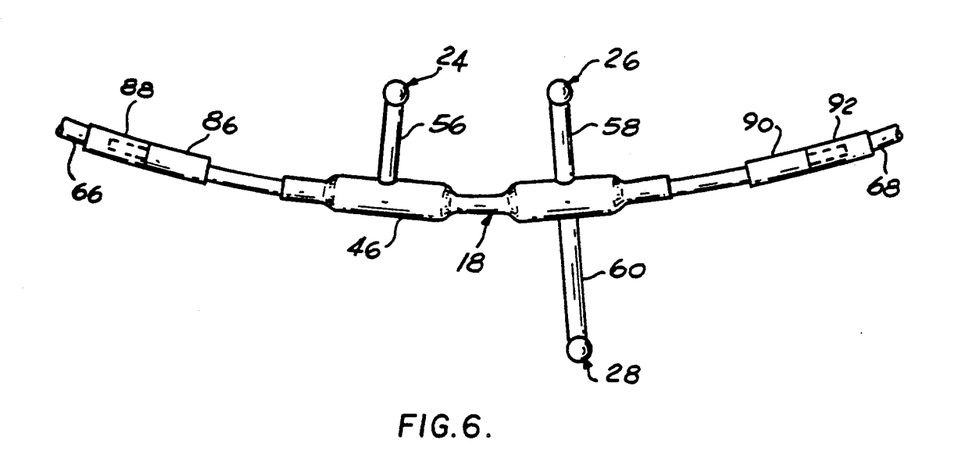

Another alternative configuration of the sensor set 10 is shown in FIG. 6. This arrangement is substantially the same as that shown in, for example, FIG. 3, with the exception that a mating pair of connectors 86 and 88 couple support structure 18 to lead wire 66, while another set of mating connectors 90 and 92 couple the support structure 18 to lead wire 68. As will be appreciated, this arrangement conveniently allows the sensor elements 16 and their associated support structure 18 to be detached from lead wires 66 and 68 and disposed of after use, avoiding the need to sterilize the product or dispose of the entire assembly prior to reuse.

Reviewing briefly the manner in which the sensor set 10 is coupled to the individual 12 for use, as shown in FIG. 1, the sensor set 10 is positioned on the upper lip of the individual 12 to obtain the desired relative positioning of junctions 24, 26, and 28 in their respective nasal and oral respiration paths. The lead wires 66 and 68 are then looped over the individual's ears and brought down under the individual's chin. There, a movable sleeve or piece of tape 94 can be used to hold the two lead wires 66 and 68 together, a retaining the sensor set 10 in place on the individual's face. The connector set 22 is then coupled to monitor 14. Given the simple, lightweight, and unobtrusive nature of the sensor set 10, any disturbance of the individual's sleep is minimized, enhancing the utility of the sensor set 10 for monitoring the individual's sleep patterns. When monitoring is completer, the sensor set 10 can be quickly and easily removed from the individual's head.

Those skilled in the art will recognize that the embodiments of the invention disclosed herein are exemplary in nature and that various changes can be made therein without departing from the scope and the spirit of the invention. In this regard, the invention is readily embodied with various types and numbers of sensor elements. Further, it will be recognized that the support structure and lead configuration can be altered in any one of a variety of ways. For example, the entire support structure could be molded as a single piece around the portion of the thermocouple wires extending between the lead wires and the exposed junction tips. In addition, the thermocouple wires could be employed as the lead wires and extended all the way to the monitor. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A sensor set, for use in monitoring the respiration of a patient, comprising:
   a first temperature-sensitive element;
   a second temperature-sensitive element;
   a third temperature-sensitive element;
   support means for supporting said first and second temperature-sensitive elements in substantially spaced-apart, parallel alignment and for supporting said first and third temperature-sensitive elements in substantially axial alignment;
   at least one pair of electrically conductive leads, coupled to said first, second, and third temperature-sensitive elements; and
   at least one pair of electrical connectors, coupled to said pair of electrically conductive leads.

2. The sensor set of claim 1, wherein said sensor set is for use in monitoring respiration through the patient's mouth and nostrils, said support means for locating said sensor set on the patient's upper lip and supporting said first and second temperature-sensitive elements adjacent separate ones of said patient's nostrils and supporting said third temperature-sensitive element adjacent the patient's mouth.

3. The sensor set of claim 2, wherein said support means includes portions of said electrically conductive leads shaped for cooperatively engaging the patient's ears to assist in the positioning of the support means on the patient's upper lip.

4. The sensor set of claim 1, wherein said first, second, and third temperature-sensitive elements comprise first, second, and third thermocouple junctions.

5. The sensor set of claim 4, further comprising a fourth thermocouple junction supported by said support means, said first, second, and third thermocouple junctions being for establishing a thermoelectrical potential relative to said fourth thermocouple junction that is representative of the temperature differential between said fourth thermocouple junction and said first, second, and third thermocouple junctions.

6. The sensor set of claim 5, wherein said fourth thermocouple junction is defined between said first, second, and third temperature-sensitive elements and one of said pair of electrically conductive leads.

7. The sensor set of claim 1, wherein said first, second, and third temperature-sensitive elements are thermistors, each one of said thermistors having a resistance that is dependent upon the temperature of the thermistor.

8. A sensor, coupleable to a monitor, for sensing the respiration of an individual, said sensor comprising:
   an elongate body;
   first respiration-responsive means, projecting radially outward from said body and exposable to the individual's respiration, for responding to said respiration;
   second respiration-responsive means, projecting radially outward from said body and exposable to the individual's respiration, for responding to said respiration;
   third respiration-responsive means, projecting radially outward from said body and exposable to the individual's respiration, for responding to said respiration; and
   a connector coupled to said first, second, and third respiration-responsive means.

9. The sensor of claim 8, wherein said first, second, and third respiration-responsive means comprises thermocouple junctions.

10. The sensor of claim 8, wherein said first, second, and third respiration-responsive means comprise thermistors.

11. The sensor of claim 8, wherein said connection means comprises a pair of electrically conductive leads coupled to said first, second, and third respiration-responsive means.

12. The sensor of claim 8, wherein said connection means comprises separate electrically conductive leads extending axially from said body and couple to said first, second, and third respiration-responsive means.

13. The sensor of claim 8, wherein said first and second respiration-responsive means further includes means for exhibiting a changing characteristic in response to said respiration.

14. The sensor of claim 8, wherein said elongate body comprises a roughly tubular element having first and second ends and wherein said connection means comprises first and second electrically conductive leads, said first electrically conductive lead extending axially from said first end of said tubular element and said second electrically conductive lead extending axially from said second end of said tubular element.

15. The sensor of claim 14, wherein said tubular element includes a reduced-diameter section spaced between said first and second ends.

* * * * *

UNITED STATES PATENT AND TRADEMARK OFFICE
CERTIFICATE OF CORRECTION

PATENT NO. : 5,069,222

DATED : December 3, 1991

INVENTOR(S) : Lewis D. McDonald, Jr.

It is certified that error appears in the above-identified patent and that said Letters Patent is hereby corrected as shown below:

| COLUMN | LINE | |
|---|---|---|
| 2 | 1 | "system" should be --systems-- |
| 2 | 25 | "addition" should be --addition,-- |
| 2 | 35 | "paterns" should be --patterns-- |
| 4 | 56 | after "between" insert --the-- |
| 5 | 22 | "partial" should be --partially-- |
| 6 | 35 | "tube" should be --tubes-- |
| 7 | 24 | "approached" should be --approach-- |
| 7 | 62 | after "together," delete "a" |
| 8 | 1 | "completer," should be --complete,-- |
| 9 | 26 | "comprises" should be --comprise-- |
| 10 | 10 | "couple" should be --coupled-- |
| [57]Abstract | 3 | "respriation" should be --respiration-- |

Signed and Sealed this

Twentieth Day of April, 1993

*Attest:*

MICHAEL K. KIRK

*Attesting Officer*  *Acting Commissioner of Patents and Trademarks*